(12) United States Patent
Edwards et al.

(10) Patent No.: US 8,455,505 B2
(45) Date of Patent: Jun. 4, 2013

(54) PYRROLOPYRIMIDINEDIONE AND ITS THERAPEUTIC USE

(75) Inventors: Christine Edwards, Flex Meadow (GB); Janus Kulagowski, Flex Meadow (GB); Harry Finch, Flex Meadow (GB)

(73) Assignee: Chiesi Farmaceutici S.p.A., Parma (IT)

( * ) Notice: Subject to any disclaimer, the term of this patent is extended or adjusted under 35 U.S.C. 154(b) by 9 days.

(21) Appl. No.: 13/146,334

(22) PCT Filed: Jan. 22, 2010

(86) PCT No.: PCT/GB2010/050092
§ 371 (c)(1),
(2), (4) Date: Oct. 17, 2011

(87) PCT Pub. No.: WO2010/086638
PCT Pub. Date: Aug. 5, 2010

(65) Prior Publication Data
US 2012/0027692 A1  Feb. 2, 2012

(30) Foreign Application Priority Data

Jan. 30, 2009 (GB) .................. 0901616.3
May 11, 2009 (GB) .................. 0908068.0

(51) Int. Cl.
*A01N 43/90* (2006.01)
*A61K 31/519* (2006.01)
*C07D 487/00* (2006.01)

(52) U.S. Cl.
USPC ....................... 514/265.1; 544/280

(58) Field of Classification Search
None
See application file for complete search history.

(56) References Cited

FOREIGN PATENT DOCUMENTS

| WO | 2007 129060 | 11/2007 |
|----|-------------|---------|
| WO | 2008 135537 | 11/2008 |
| WO | 2009 013444 | 1/2009 |

OTHER PUBLICATIONS

International Search Report issued Apr. 12, 2010 in PCT/GB10/050092 filed Jan. 22, 2010.

*Primary Examiner* — Jeffrey Murray
(74) *Attorney, Agent, or Firm* — Oblon, Spivak, McClelland, Maier & Neustadt, L.L.P.

(57) ABSTRACT

The compound of formula (I) is an inhibitor of human neutrophil elastase, useful for inhalation treatment of pulmonary inflammation.

20 Claims, No Drawings

PYRROLOPYRIMIDINEDIONE AND ITS THERAPEUTIC USE

CROSS-REFERENCE TO RELATED APPLICATIONS

The present application is a 35 U.S.C. §371 National Stage patent application of International patent application PCT/GB2010/050092, filed on Jan. 22, 2010, which claims priority to Great Britain patent applications GB 0908068.0, filed on May 11, 2009 and GB 0901616.3, filed on Jan. 30, 2009.

FIELD OF THE INVENTION

This invention relates to a specific substituted 3,4,6,7-tetrahydro-1H-pyrrolo[3,4-d]pyrimidine-2,5-dione compound which is an inhibitor of human neutrophil elastase, and to its use in therapy of respiratory diseases by inhaled administration.

BACKGROUND TO THE INVENTION

Human neutrophil elastase (HNE) is a 32 kDa serine proteinase found in the azurophilic granules of neutrophils. It has a role in the degradation of a wide range of extracellular matrix proteins, including fibronectin, laminin, proteoglycans, Type III and Type IV collagens as well as elastin (Bieth, G. In *Regulation of Matrix accumulation*, Mecham, R. P. (Eds), Academic Press, NY, USA 1986, 217-306). HNE has long been considered to play an important role in homeostasis through repair and disposal of damaged tissues via degradation of the tissue structural proteins. It is also relevant in the defence against bacterial invasion by means of degradation of the bacterial body. In addition to its effects on matrix tissues, HNE has been implicated in the upregulation of IL-8 gene expression and also induces IL-8 release from the epithelial cells of the lung. In animal models of Chronic Obstructive Pulmonary Disease induced by tobacco smoke exposure both small molecule inhibitors and protein inhibitors of HNE inhibit the inflammatory response and the development of emphysema (Wright, J. L. et al. *Am. J. Respir. Crit. Care Med.* 2002, 166, 954-960; Churg, A. et al. *Am. J. Respir. Crit. Care Med.* 2003, 168, 199-207). Thus, HNE may play a role both in matrix destruction and in amplifying inflammatory responses in chronic respiratory diseases where neutrophil influx is a characteristic feature. Indeed, HNE is believed to play a role in several pulmonary diseases, including chronic obstructive pulmonary disease (COPD), cystic fibrosis (CF), acute respiratory distress syndrome (ARDS), pulmonary emphysema, pneumonia and lung fibrosis. It is also implicated in several cardiovascular diseases in which tissue remodelling is involved, for example, in heart failure and the generation of ischaemic tissue injury following acute myocardial infarction.

COPD is an umbrella term encompassing three different pathological conditions, all of which contribute to limitation of airflow: chronic bronchitis, emphysema and small-airway disease. Generally all three will exist to varying extents in patients presenting with COPD, and all three may be due to neutrophil-mediated inflammation, as supported by the increased number of neutrophils observed in bronchoalveolar leakage (BAL) fluids of COPD patients (Thompson, A. B.; Daughton, D.; et al. *Am. Rev. Respir. Dis.* 1989, 140, 1527-1537). The major pathogenic determinant in COPD has long been considered to be the protease-anti-protease balance (also known as the 'elastase:anti-elastase hypothesis'), in which an imbalance of HNE and endogenous antiproteases such as α1-antitrypsin ($\alpha_1$-AT), Secretory leukocyte protease inhibitor (SLPI) and pre-elafin leads to the various inflammatory disorders of COPD. Individuals that have a genetic deficiency of the protease inhibitor a 1-antitrypsin develop emphysema that increases in severity over time (Laurrell, C. B.; Erikkson, S Scand. *J. Clin. Invest.* 1963 15, 132-140). An excess of HNE is therefore destructive, leading to the breakdown of pulmonary morphology with loss of elasticity and destruction of alveolar attachments of airways in the lung (emphysema) whilst simultaneously increasing microvascular permeability and mucus hypersecretion (chronic bronchitis).

International patent publication WO2007/129060 relates, inter alia, to homodimeric or heterodimeric compounds of formula M-L-M$^1$ wherein L is a divalent linker radical and M and M$^1$ are each independently a radical of formula (A') or (B'):

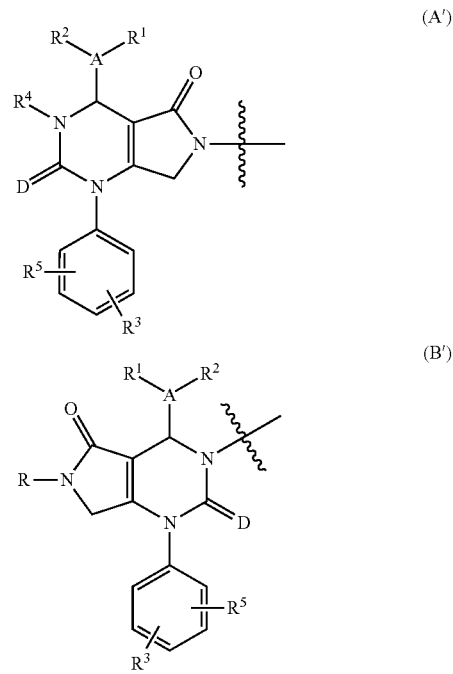

wherein
A is aryl or heteroaryl;
D is oxygen or sulphur;
$R^1$, $R^2$, $R^3$ and $R^5$ are independently each hydrogen, halogen, nitro, cyano, $C_1$-$C_6$-alkyl, $C_2$-$C_6$-alkenyl, $C_2$-$C_6$-alkynyl, hydroxy or $C_1$-$C_6$-alkoxy or $C_2$-$C_6$-alkenyloxy, wherein $C_1$-$C_6$-alkyl and $C_1$-$C_6$-alkoxy can be further substituted with one to three identical or different radicals selected from the group consisting of halogen, hydroxy and $C_1$-$C_4$-alkoxy;
R and $R^4$ each independently represent a radical of formula —[X]$_m$—[Alk$^1$]$_p$-[Q]$_n$-[Alk$^2$]$_q$-[X$^1$]$_k$-Z wherein
k, m, n, p and q are independently 0 or 1;
Alk$^1$ and Alk$^2$ each independently represent an optionally substituted $C_1$-$C_6$ alkylene, or $C_2$-$C_6$ alkenylene radical which may optionally contain an ether (—O—), thioether (—S—) or amino (—NR$^A$—) link wherein R$^A$ is hydrogen or $C_1$-$C_3$ alkyl;
Q represents (i) —O—, —S—, —S(=O)—, —S(=O)$_2$—, —S$^+$(R$^A$)—, —N(R$^A$)—, —N$^+$(R$^A$)(R$^B$)—, —C(=O)—, —C(=O)O—, —OC(=O)—, —C(=O) NR$^A$—, —NR$^A$C(=O)—, —S(O$_2$)NR$^A$—, —NR$^A$S(O$_2$)—, —NR$^A$C(=O)NR$^B$—, —NR$^A$C(=NR$^A$)NR$^B$—, —C(=NR$^D$)NR$^E$—, —NR$^E$C(=NR$^D$)—, wherein R$^A$, R$^B$, R$^D$ and R$^E$ are independently hydrogen, C$_1$-C$_6$ alkyl, or C$_3$-C$_6$ cycloalkyl, or R$^A$ and R$^B$, or R$^D$ and R$^E$ taken together with the nitrogen to which they are attached form a monocyclic heterocyclic ring of 5 to 7 ring atoms which my contain a further heteroatom selected from N, O and S, or (ii) an optionally substituted divalent mono- or bicyclic carbocyclic or heterocyclic radical having 3-6 ring members;

X represents —(C=O)—, —S(O$_2$)—, —C(=O)O—, —(C=O)NR$^A$—, or —S(O$_2$)NR$^A$—, wherein R$^A$ is hydrogen, C$_1$-C$_6$ alkyl, or C$_3$-C$_6$ cycloalkyl;

X$^1$ represents —O—, —S—, or —NH; and

Z is hydrogen or an optionally substituted mono- or bicyclic carbocyclic or heterocyclic radical having 3-6 ring members.

BRIEF DESCRIPTION OF THE INVENTION

This invention relates to a compound within the scope of the claims of WO2007/129060 but not specifically disclosed therein. Like the compounds of WO2007/129060, the present compound is particularly useful for pulmonary application by inhalation, for treatment of inflammatory disease of the lung and respiratory tract. However, the present compound has the advantage of a shorter residence time in the lung, expressed as its half life (T½), compared with its closest structural analogue disclosed in WO2007/129060, leading to the desirable characteristic of earlier clearance on cessation of treatment.

DETAILED DESCRIPTION OF THE INVENTION

The present invention provides a compound of formula (I) and pharmaceutically acceptable salts thereof:

(I)

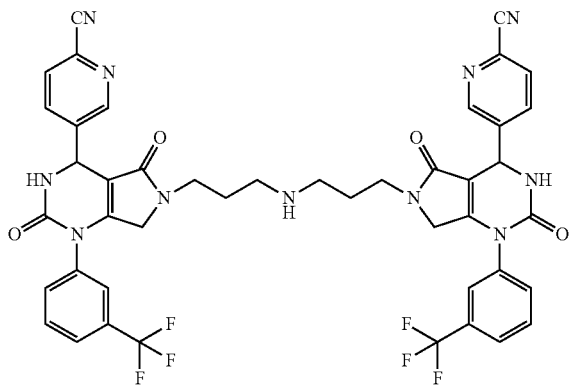

For a review on salts, see *Handbook of Pharmaceutical Salts: Properties, Selection, and Use* by Stahl and Wermuth (Wiley-VCH, Weinheim, Germany, 2002). Pharmaceutically acceptable salts of the compound of the invention include acid addition salts such as a hydrochloride, hydrobromide, phosphate, sulfate, acetate, diacetate, fumarate, maleate, tartrate, citrate, oxalate, methanesulfonate or p-toluenesulfonate.

It is expected that the compound of the invention may be isolated as one or more hydrates or solvates, and in single or multiple crystalline polymorphic forms. Any reference herein, including the claims herein, to "compound with which the invention is concerned" or "compound of the invention" or "the present compound", or "compounds of formula (I)" and the like, includes reference to salts, hydrates, and solvates of such compounds, and crystal forms thereof.

The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

The compound of the invention has two chiral centres indicated by asterisks as follows:

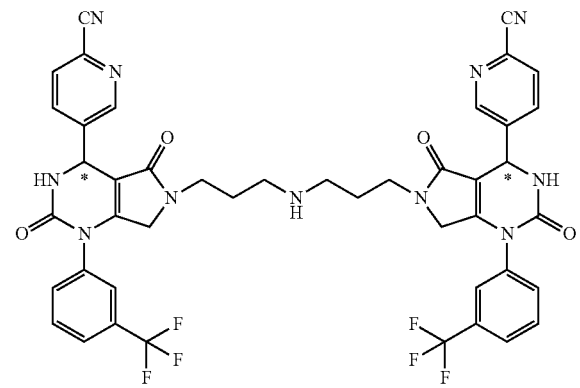 [SMILES: N#Cc1ccc(C2NC(=O)N(c3cccc(C(F)(F)F)c3)C3=C2C(=O)N(CCCNCCCN2CC4=C(C2=O)C(c2ccc(C#N)nc2)NC(=O)N4c2cccc(C(F)(F)F)c2)C3)cn1]

Preferably the compound of the invention has predominantly the R-R configuration, (shown in formula (IA)) at those centres, rather than the R-S and/or S-S configuration.

(IA)

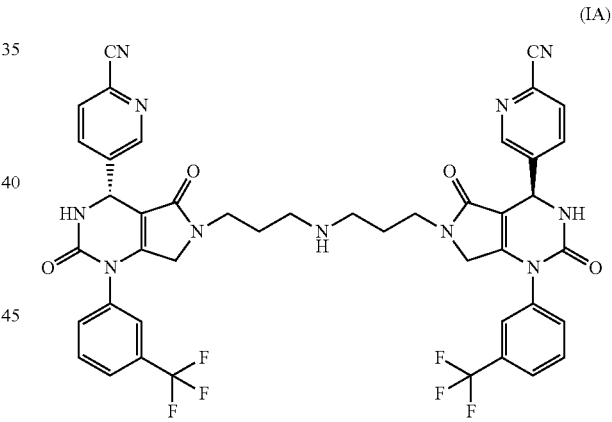

Thus preferred samples of the compound of the invention predominantly contain the R-R diastereomer. For example, samples of the compound of the invention may consist of at least 90%, preferably at least 95%, and more preferably 98% or more, by weight of the R-R diastereomer as depicted in of formula (IA), and less than 10%, 5%, or 2% by weight respectively of other diastereomers.

The compound of the invention is intended for pulmonary administration for the treatment or prevention of respiratory tract diseases in which HNE is implicated, for example chronic obstructive pulmonary disease (COPD), chronic bronchitis, lung fibrosis, pneumonia, acute respiratory distress syndrome (ARDS), pulmonary emphysema, smoking-induced emphysema or cystic fibrosis, asthma, and rhinitis. Thus, compounds of the invention may be used in a method of therapy, for the treatment of a patient suffering from a respiratory tract condition or disease as defined above.

Hence another aspect of the invention is a pharmaceutical composition adapted for pulmonary administration by inhalation, comprising the compound of the invention and one or more pharmaceutically acceptable carriers or excipients. As explained above, the pharmaceutical compositions of the invention include those wherein the compound of the invention is predominantly present as the R—R diastereomer (relative to the S-S and R-S diastereomers). Preferably the compositions of the invention contain the compound of formula (I) as at least 90%, or at least 95%, or at least 98% or more by weight of the R-R diastereomer, and less than 10%, 5% or 2% respectively by weight of other diastereomers.

Compositions suitable for administration by pulmonary inhalation are known, and may include carriers and/or diluents that are known for use in such compositions. The composition may contain 0.01-99% by weight of active compound. Preferably, a unit dose comprises the active compound in an amount of 1 µg to 10 mg.

The most suitable dosage level may be determined by any suitable method known to one skilled in the art. It will be understood, however, that the specific amount for any particular patient will depend upon a variety of factors, including the activity of the specific compound that is used, the age, body weight, diet, general health and sex of the patient, time of administration, the route of administration, the rate of excretion, the use of any other drugs, and the severity of the disease undergoing treatment. In general, the daily dose range will lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases.

For delivery by inhalation, the active compound is preferably in the form of microparticles. They may be prepared by a variety of techniques, including spray-drying, freeze-drying and micronisation.

By way of example, a composition of the invention may be prepared as a suspension for delivery from a nebuliser or as an aerosol in a liquid propellant, for example for use in a pressurised metered dose inhaler (PMDI). Propellants suitable for use in a PMDI are known to the skilled person, and include CFC-12, HFA-134a, HFA-227, HCFC-22 ($CCl_2F_2$) and HFA-152 ($CH_4F_2$ and isobutane).

In a preferred embodiment of the invention, a composition of the invention is in dry powder form, for delivery using a dry powder inhaler (DPI). Many types of DPI are known.

Microparticles for delivery by inhalation may be formulated with excipients that aid delivery and release. For example, in a dry powder formulation, microparticles may be formulated with large carrier particles that aid flow from the DPI into the lung. Suitable carrier particles are known, and include lactose particles; they may have a mass median aerodynamic diameter of greater than 90 µm.

Aerosol generation can be carried out using, for example, pressure-driven jet atomizers or ultrasonic atomizers, preferably using propellant-driven metered aerosols or propellant-free administration of micronized active compounds from, for example, inhalation capsules or other "dry powder" delivery systems.

The active compound may be dosed as described depending on the inhaler system used. In addition to the active compounds, the administration forms may additionally contain excipients, such as, for example, propellants (e.g. Frigen in the case of metered aerosols), surface-active substances, emulsifiers, stabilizers, preservatives, flavorings, fillers (e.g. lactose in the case of powder inhalers) or, if appropriate, further active compounds.

For the purposes of inhalation, a large number of systems are available with which aerosols of optimum particle size can be generated and administered, using an inhalation technique which is appropriate for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhalers for example as described EP-A-0505321).

In the case of an aerosol-based formulation, a preferred composition is:

| | |
|---|---|
| Compound of the invention | 24 mg/canister |
| Lecithin, NF Liq. Conc. | 1.2 mg/canister |
| Trichlorofluoromethane, NF | 4.025 g/canister |
| Dichlorodifluoromethane, NF | 12.15 g/canister. |

The compound of the invention may be used in combination with other drugs that are used in the treatment/prevention/suppression or amelioration of the diseases or conditions for which present compounds are useful. Such other drugs may be administered, by a route and in an amount commonly used therefore, contemporaneously or sequentially with a compound of the invention. When a compound of the invention is used contemporaneously with one or more other drugs, a pharmaceutical composition containing such other drugs in addition to the compound of the invention is preferred. Accordingly, the pharmaceutical compositions of the present invention include those that also contain one or more other active ingredients, in addition to the compound of the invention.

Suitable therapeutic agents for a combination therapy with the compound of the invention include: (1) a corticosteroid, for example fluticasone or budesonide; (2) a β2-adrenoreceptor agonist, for example salmeterol or formeterol; (3) a leukotriene modulator, for example montelukast or pranlukast; (4) anticholinergic agents, for example selective muscarinic-3 (M3) receptor antagonists such as tiotropium bromide; (5) a dual muscarinic-3 (M3) receptor antagonist/β2-adrenoreceptor agonist such as GSK 961081; (6) phosphodiesterase-IV (PDE-IV) inhibitors, for example roflumilast or cilomilast; (7) an antitussive agent, such as codeine or dextramorphan; (8) a non-steroidal anti-inflammatory agent (NSAID), for example ibuprofen or ketoprofen; (9) a mucolytic, for example N acetyl cysteine or fudostein; (10) a expectorant/mucokinetic modulator, for example ambroxol, hypertonic solutions (e.g. saline or mannitol) or surfactant; (11) a peptide mucolytic, for example recombinant human deoxyribonuclease I (dornase-alfa and rhDNase) or helicidin; and (12) antibiotics, for example azithromycin, tobramycin and aztreonam.

The invention is further explained in the following Examples:

A. Synthesis of the Compound of the Invention

The routes shown in Schemes 1 to 3 describe alternative routes for the synthesis of Compound (IA). The Biginelli reaction between 2-bromopyridine-5-carboxaldehyde, (3-trifluoromethylphenyl)urea and an alkyl or aryl acetoacetate e.g. methyl acetoacetate, forming compound (1) may be carried out in the presence of a catalyst such as polyphosphoric acid. Replacement of the bromine atom with a cyano group can be achieved using various standard cyanation reaction conditions e.g. acetone cyanohydrin with copper catalysis. Chiral separation of the enantiomers of (2) can be achieved using chiral HPLC. Bromination of the (R)-enantiomer (3a) using bromine, or other standard brominating reagent, may then provide (4) (Scheme 1).

Scheme 1

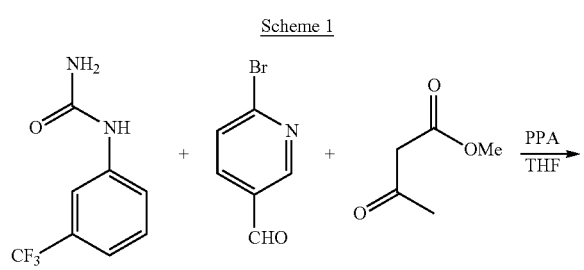

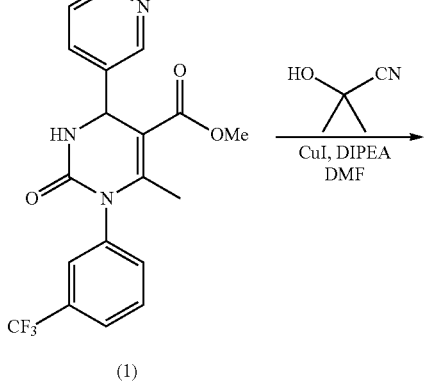

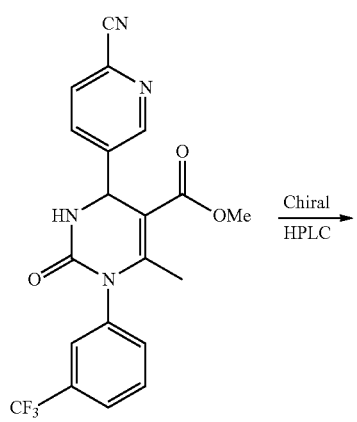

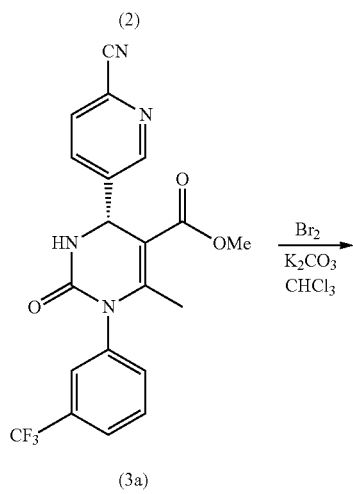

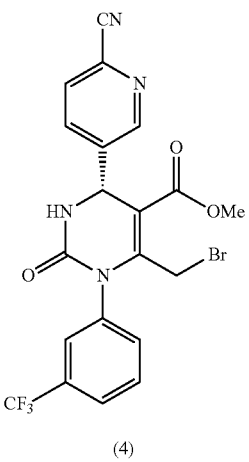 [SMILES: COC(=O)C1=C(CBr)N(c2cccc(C(F)(F)F)c2)C(=O)N[C@@H]1c1ccc(C#N)nc1]

Alternatively (Scheme 2), a Biginelli reaction between an ester of 5-formylpyridine-2-carboxylic acid, an alkyl or aryl acetoacetate and (3-trifluoromethylphenyl) urea in the presence of a catalyst such as polyphosphoric acid may be used. Specifically, methyl 5-formylpyridine-2-carboxylate (5), which can be prepared by carbonylation of 2-bromopyridine-5-carboxaldehyde in the presence of methanol, can be reacted with methyl acetoacetate and (3-trifluoromethylphenyl) urea to give compound (6). Conversion to the carboxylic acid (7) can be achieved using standard hydrolysis conditions e.g. aqueous sodium hydroxide. Formation of a diastereomeric mixture of salts by treatment of (7) with (+)-cinchonine, and crystallisation of the (R)-enantiomer preferentially from ethanol, allows the isolation of (8) after treatment with acid. For the formation of amide (9), reactions may be accomplished using standard conditions, for example treatment of the acid (8) with carbonyldiimidazole followed by reaction with ammonia. The bromination of (8) to give (10) may be achieved using, for example, bromine or N-bromosuccinimide. Intermediate (9) may alternatively be converted into intermediate (3), which is useful in the alternative pathway (Scheme 1), by dehydration.

Scheme 2

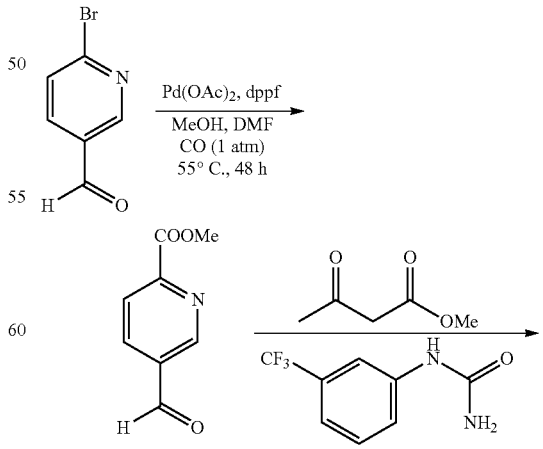

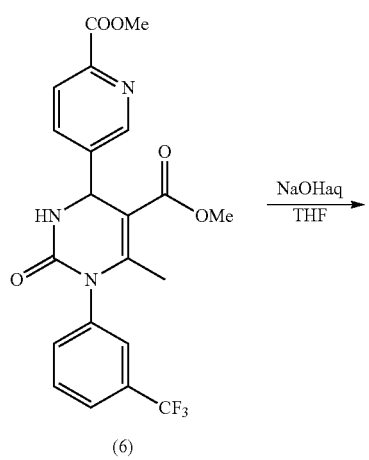

(6)

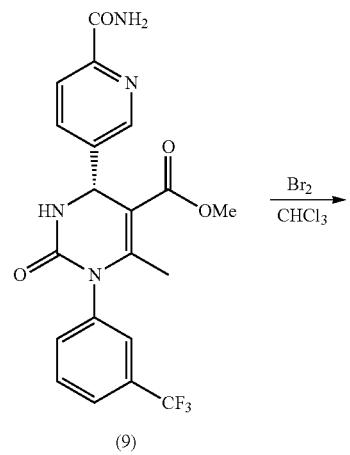

(9)

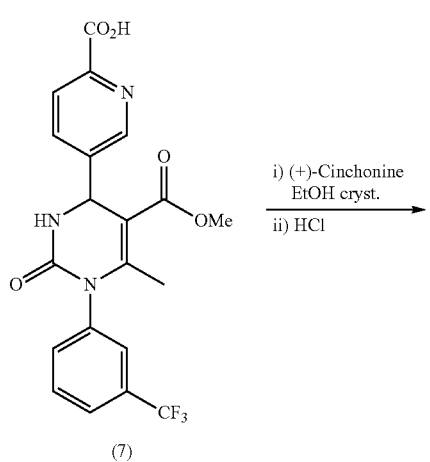

(7)

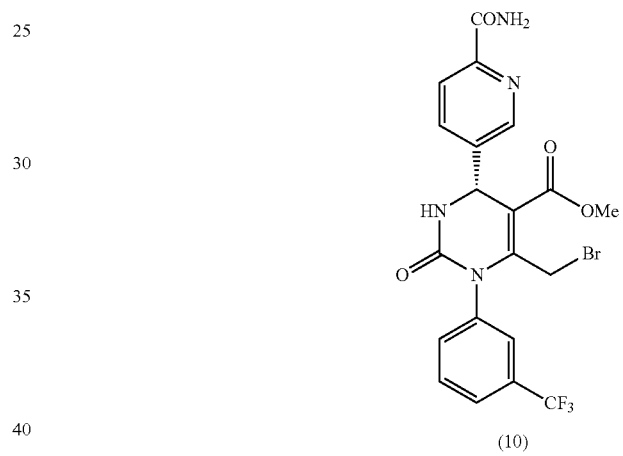

(10)

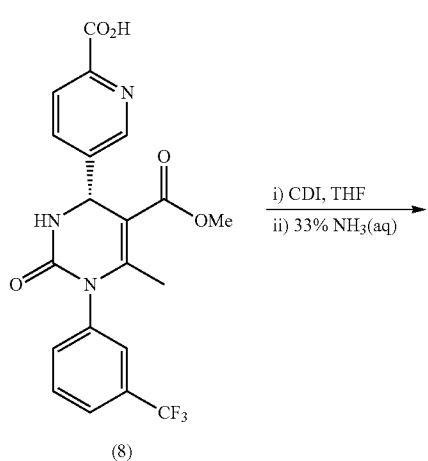

(8)

Scheme 3 shows that both compounds (4) and (10) may be converted into compound (IA). The dimerisation reaction with bis-(3-aminopropyl)amine may benefit from the use of a suitable base e.g. triethylamine, NaHCO₃, DIPEA etc and bis-(3-aminopropyl)amine may be used in a protected form i.e. the secondary amine may be protected by e.g. tert-butyloxycarbonyl, benzyloxycarbonyl, etc. with the protecting group being removed at a later stage. Compound (II), the product from the reaction of (10) with bis-(3-aminopropyl) amine may be dehydrated to give (IA) whilst (4) reacts directly with bis-(3-aminopropyl)amine to give (IA). Compound (IA) may be obtained as the free base by chromatography and then converted into a salt by treatment with a suitable acidic compound. Alternatively, (IA) may be obtained by crystallisation as a suitable salt, e.g. the 4-toluenesulphonate, from the crude dimerisation reaction of (4). All of the reactions may be performed in various solvents that must be compatible with the reagents used, and may be carried out at various suitable temperatures, typically 0-80° C.

Scheme 3

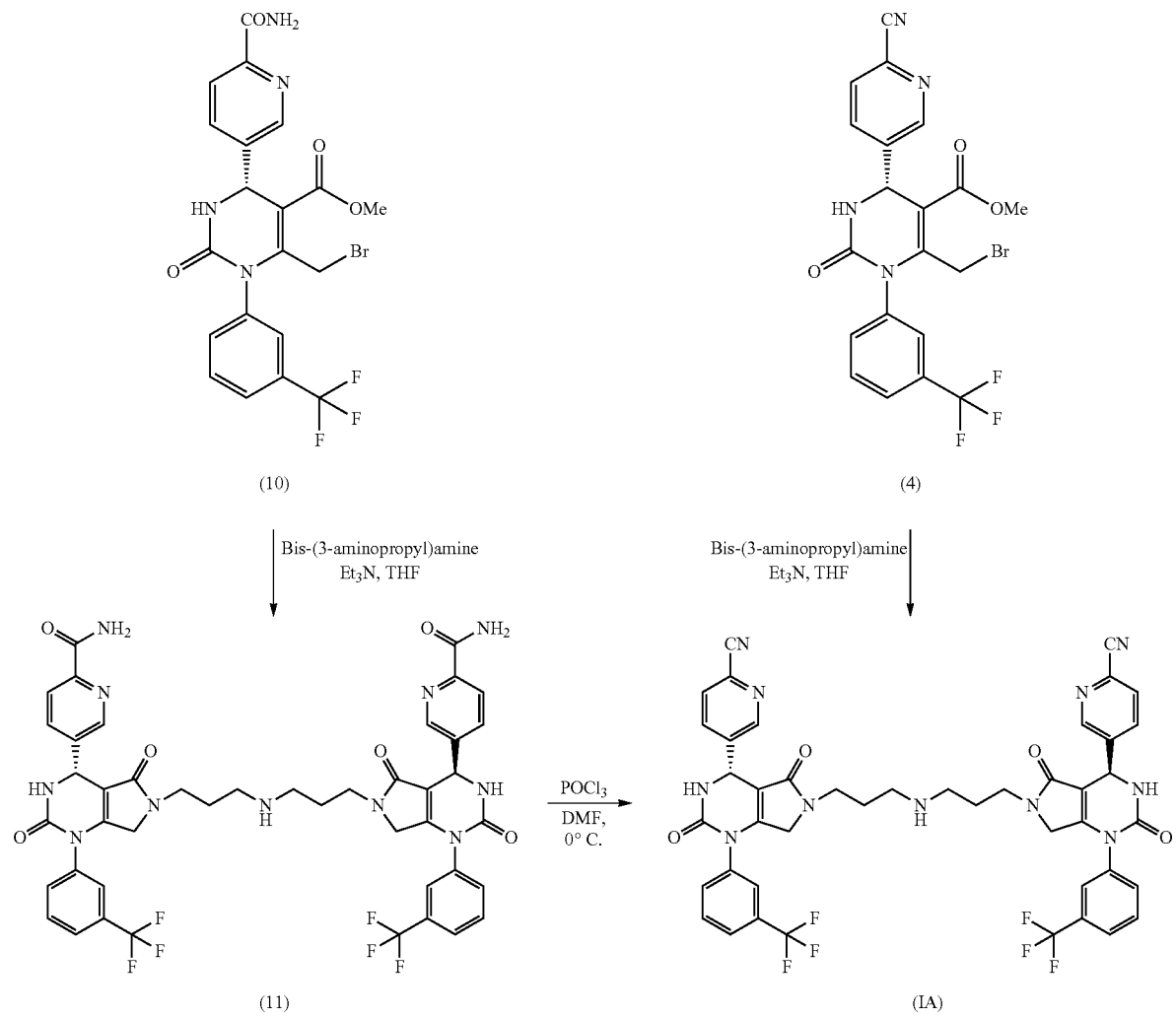

General Methods

Reactions were not carried out under an inert atmosphere unless specified. Where products were purified by column chromatography on silica, 'silica' refers to silica gel for chromatography, 0.035 to 0.070 mm (230 to 400 mesh), and an applied pressure of nitrogen up to 10 p.s.i for accelerated column elution. Where separation was carried out using a RediSep® Si cartridge, an automated chromatography system was used (CombiFlash® companion) together with a pre-packed polypropylene (RediSep®) column containing silica with average particle size 35-70 µm (230-400 mesh). All solvents and commercial reagents were used as received.

Analytical LC-MS Methods

LC-MS Method 1

Waters Micromass ZMD with a C18-reverse-phase column (30×4.6 mm Phenomenex Luna 3 µm particle size), elution with A: water+0.1% formic acid; B: methanol+0.1% formic acid. Gradient:

| Gradient - Time | flow ml/min | % A | % B |
|---|---|---|---|
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Detection-MS, ELS, UV (200 µl split to ESI source with inline Waters 996 DAD detection)

MS ionisation method—Electrospray (positive and negative ion)

LC-MS Method 2

Waters Micromass ZMD with a C18-reverse-phase column (30×4.6 mm Phenomenex Luna 3 µm particle size), elution with A: water+0.1% formic acid; B: acetonitrile+0.1% formic acid. Gradient:

| Gradient - Time | flow ml/min | % A | % B |
| --- | --- | --- | --- |
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Detection—MS, ELS, UV

MS ionisation method—Electrospray (positive and negative ion)

LC-MS Method 3

Waters Quattro Micro with a C18 LC column (100×3.0 mm Higgins Clipeus 5 μm particle size), elution with A: water+ 0.1% formic acid; B: methanol+0.1% formic acid. Gradient:

| Gradient - Time | flow ml/min | % A | % B |
| --- | --- | --- | --- |
| 0.00 | 1.0 | 85 | 15 |
| 1.00 | 1.0 | 85 | 15 |
| 13.00 | 1.0 | 5 | 95 |
| 20.00 | 1.0 | 5 | 95 |
| 22.00 | 1.0 | 85 | 15 |
| 25.00 | 1.0 | 85 | 15 |

Detection-MS, ELS, UV (100 μl split to MS with in-line UV detector)

MS ionisation method—Electrospray (positive and negative ion)

LC-MS Method 4

Waters Micromass ZQ2000 with a C18-reverse-phase column (100×2.1 mm Acquity BEH with 1.7 μm particle size) maintained at 40° C., elution with A:water+0.1% formic acid; B: acetonitrile+0.1% formic acid. Gradient:

| Gradient - Time | flow ml/min | % A | % B |
| --- | --- | --- | --- |
| 0.00 | 0.4 | 95 | 5 |
| 0.40 | 0.4 | 95 | 5 |
| 6.00 | 0.4 | 5 | 95 |
| 6.80 | 0.4 | 5 | 95 |
| 7.00 | 0.4 | 95 | 5 |
| 8.00 | 0.4 | 95 | 5 |

Detection—MS, UV PDA

MS ionisation method—Electrospray (positive/negative ion)

Chiral LC Methods

Chiral LC Method 1 (analytical)

CHIRALPAK® IC 5 μm–250×4.6 mm eluting with 10% n-heptane, 90% EtOH, 0.1% diethylamine. Flow rate=0.7 ml/min. UV detection at 250 nm.

Chiral LC Method 2 (preparative)

CHIRALPAK® IC 20 μm–250×76 mm eluting with 30% n-heptane, 70% EtOAc, 0.1% diethylamine. Flow rate=270 ml/min. UV detection at 330 nm.

Chiral LC Method 3 (analytical)

CHIRALPAK® IA 5 μm–250×4.6 mm eluting with 20% IPA, 80% n-heptane, 0.1% TFA. Flow rate=1 ml/min. UV detection at 254 nm.

Melting Point Determination

Melting points were determined using a Buchi B-540 apparatus.

Optical Rotation $[\alpha]_D^{25}$ values were obtained on an Optical Activity Ltd AA-10R automatic polarimeter using a 25 mm cell and a sodium lamp as source. Samples were run in methanol at approximately 1% w/v. Measurements were taken in duplicate.

Differential Scanning Calorimetry (DSC)

DSC measurements were performed on a Mettler Toledo DSC823e equipped with a Mettler Toledo TS0801RO sample robot and automated sample carousel. Samples were prepared in 40 μl aluminium pans, the sample lids were automatically pierced by the robot and the analysis undertaken between 30 and 250° C. at 10° C./min. Typically, 1-3 mg were used for analysis and the experiment was performed under dry nitrogen purged at 50 mlmin$^{-1}$. The instrument was calibrated for energy and temperature using certified indium.

X-Ray Powder Diffractometers (XRPD)

System 1

The data was collected using a Siemens D5000 diffractometer using Cu Kα radiation (40 kV, 40 mA), θ-θ goniometer, divergence of V20 and receiving slits, a graphite secondary monochromator and a scintillation counter. The instrument was performance checked using a certified Corundum standard (NIST 1976). The software used for data collection was Diffrac Plus XRD Commander v2.3.1 and the data were analysed and presented using Diffrac Plus EVA v 11.0.0.3. Samples were run under ambient conditions as flat plate specimens using powder as received. The sample was gently packed into a cavity cut into polished, zero-background (510) silicon wafer. The sample was rotated in its own plane during analysis. The data was collected between 2 to 42 °2θ, using a step size of 0.05 °2θ and a collection time of 4 s.step$^{-1}$ System 2

The data was collected using a Bruker D8 diffractometer using Cu Kα radiation (40 kV, 40 mA), 8-28 goniometer, with a Lynxeye detector fitted with a Ge monochromator. The instrument was performance checked using a certified Corundum standard (NIST 1976). The software used for data collection was Diffrac Plus XRD Commander v2.5.0 and the data were analysed and presented using Diffrac Plus EVA v 11.0.0.2 or v 13.0.0.2. Samples are run under ambient conditions as flat plate specimens using powder as received. The data was collected between 2 to 42 °2θ, using a step size: 0.05 °2θ and a collection time of 0.5 s.step$^{-1}$.

Dynamic Vapour Sorption (DVS)

DVS analysis was performed on a Surface Measurement Systems (SMS) DVS-Intrinsic moisture sorption analyser. The instrument was controlled by SMS Analysis Suite software (DVS-Intrinsic Control v1.0.0.30). Analysis of the data was performed using Microsoft Excel 2007 together DVS Standard Analysis Suite (v6.0.0.7). Sample temperature was maintained at 25° C. and the sample humidity was obtained by mixing streams of wet and dry nitrogen at a total flow rate of 200 mlmin$^{-1}$. The relative humidity was measured using a calibrated Rotronic probe (dynamic range 1-100% relative humidity (RH)) located close to the sample. The weight change of the sample as a function of % RH was constantly monitored by the microbalance (accuracy±0.005 mg). 20 mg of sample was then placed in a tared stainless steel mesh basket under ambient conditions. The sample was loaded and unloaded at 40% RH and 25° C. (typical room conditions) and the sample subjected to a graduated DVS regime over 2 cycles using the parameters shown in Table 1. A DVS isotherm was calculated from this data.

TABLE 1

| Method parameters for DVS experiment | |
|---|---|
| Parameter | Setting |
| Sorption - cycle 1 (% RH) | 40-90 |
| Desorption - cycle 1 (% RH) | 90-0 |
| Sorption - cycle 2 (% RH) | 0-90 |
| Desorption - cycle 2 (% RH) | 90-0 |
| Sorption - cycle 3 (% RH) | 0-40 |
| Intervals (% RH) | 10 |
| dmdt (% min$^{-1}$) | 0.002 |
| Sample temperature (° C.) | 25 |

Single Crystal X-Ray

Single crystal x-ray analysis was performed on a Bruker-Nonius FR591 rotating anode system fitted with a Bruker-Nonius Roper CCD camera using X-rays at 0.71073 angstroms from MoK using a graphite monochromator. Data was collected at a temperature of 120K. Data collection was using COLLECT (Hooft, R. W. W., 1998), Cell refinement by DENZO (Otwinowski & Minor, 1997) & COLLECT (Hooft, R. W. W., 1998). Structure solution and refinement by SHELX (Sheldrick, 2008).

NMR Spectrometers

NMRs were run on either a Varian Unity Inova 400 MHz spectrometer or a Bruker Avance DRX 400 MHz spectrometer.

Abbreviations used in the experimental section:
DCM=dichloromethane
DIPEA=di-isopropylethylamine
DMF=N,N-dimethylformamide
RT=room temperature
Rt=retention time
TFA=trifluoroacetic acid
THF=tetrahydrofuran Intermediate 1

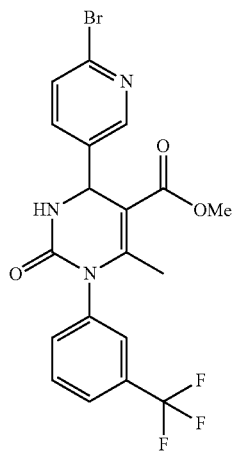 [SMILES: COC(=O)C1=C(C)N(c2cccc(C(F)(F)F)c2)C(=O)NC1c1ccc(Br)nc1]

2-Bromopyridine-5-carboxaldehyde (170.0 g, 913 mmol), (3-trifluoromethylphenyl)-urea (185 g, 906 mmol) and methyl acetoacetate (106 g, 913 mmol) were added to a stirred suspension of polyphosphoric acid (500 g) in dry THF (1500 ml) and the reaction was stirred at reflux for 5 hours. The solution was cooled to RT and poured into water (2.5 l). The product was extracted into ethyl acetate and the aqueous layer was re-extracted with ethyl acetate. The combined organic layers were washed with water, then with brine and dried over anhydrous sodium sulphate. The solvent was evaporated to give an orange gum which was dissolved in a minimum volume of diethyl ether and left to crystallize. The product was a white solid.

Yield: 283.3 g (66%)
LC-MS (Method 1): Rt=3.83 min, m/z=470/472 [M+H]$^+$

Intermediate 2

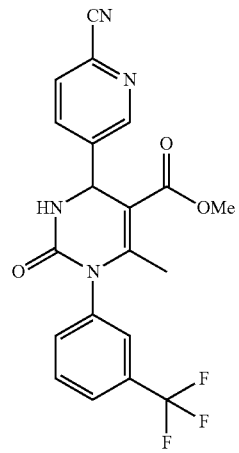 [SMILES: COC(=O)C1=C(C)N(c2cccc(C(F)(F)F)c2)C(=O)NC1c1ccc(C#N)nc1]

A three necked flask was charged with Intermediate 1 (128.0 g, 271 mmol), cuprous iodide (58.2 g, 310 mmol) and DMF (1250 ml). The reaction mixture was heated with stirring until the internal reaction temperature reached 50° C. Acetone cyanohydrin (45 ml, 178 mmol) and DIPEA (83.7 ml, 178 mmol) were then added and the reaction mixture was allowed to heat to 150° C. and stirred for 6 hours. The solution was cooled to RT and diluted with DCM (2.5 l) The solution was washed with water (×3) and brine (×1), then dried over anhydrous sodium sulphate. After filtration and removal of the solvent under high vacuum, the crude material was purified by flash chromatography on silica gel (230-400 mesh) eluting with diethyl ether to afford the title product as white solid.

Yield=74.2 g (65%)
LC-MS (Method 1): Rt=4.06 min, m/z=417 [M+H]$^+$

Intermediate 3a (R)-enantiomer

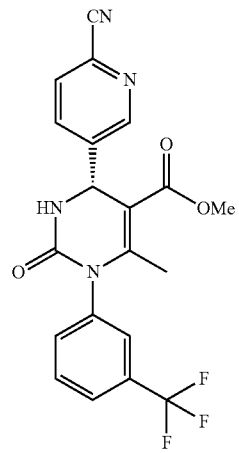 [SMILES: COC(=O)C1=C(C)N(c2cccc(C(F)(F)F)c2)C(=O)N[C@@H]1c1ccc(C#N)nc1]

Method 1

Intermediate 2 (53.1 g) was separated into two enantiomers using Chiral LC Method 2.

Intermediate 3a (R)-enantiomer [Stereochemistry determined by X-ray crystallography of bromination product (Intermediate 4)]

Recovery=26.0 g (49%)
HPLC (Chiral LC Method 1): 5.8 min (>98.6% ee)
Optical rotation $[\alpha]_D^{25}$ −12.8°

Intermediate 3b (S)-enantiomer also recovered
Recovery=23.8 g (45%)
HPLC (Chiral LC Method 1): 10.0 min (>99.5% ee)
Optical rotation $[\alpha]_D^{25}$ +10.6°

Method 2

Intermediate 9 (140 mg, 0.32 mmol) was dissolved in DCM (1.5 ml) and DMF (0.05 ml, catalytic) was added, followed by phosphorus oxychloride (0.3 ml, 3.2 mmol). The mixture was left to stand at RT for 3 days, then quenched with water and the product extracted into ethyl acetate. The organic layer was washed with water, then with brine and dried over anhydrous sodium sulphate. The drying agent was filtered off and the solution was evaporated to dryness yielding a brown foam. This was purified by on a RediSep® Si cartridge using 50-100% ethyl acetate/pentane as eluent. Appropriate fractions were combined to yield the required product as a pale foam.

Yield: 19 mg (14%)
LC-MS (Method 1): Rt=4.04 min, m/z=417.29 [M+H]$^+$
Optical rotation $[\alpha]_D^{25}$ −10.0°. Stereochemistry confirmed as (R) by comparison with Intermediate 3a prepared by Method 1.

Intermediate 4

A solution of bromine (41.6 g, 260 mmol) in chloroform (200 ml) was added dropwise over 30 min to a stirred solution of Intermediate 3a (104 g, 250 mmol) in chloroform (1 l) containing solid potassium carbonate (74.0 g, 530 mmol). After stirring for 1 h, the suspension was filtered and the solvent was removed under reduced pressure to leave a pale yellow foam. This was dissolved in a minimum volume of ethyl acetate and diluted with diethyl ether. The product crystallized as a white solid, which was filtered off, washed with 10% ethyl acetate/diethyl ether and dried in vacuo.

Yield=54 g (44%). A second crop brought the yield up to 85%
LC-MS (Method 2): Rt=4.19 min, m/z=495/497 [M+H]$^+$ The stereochemistry was confirmed as (R) by single crystal X-ray crystallography with a space group P1 triclinic, R factor of 0.0518, GOF 1.038, Flack parameter 0.042 (sd±0.007) and Hooft Parameter 0.083 (sd±0.007).

Intermediate 5

2-Bromopyridine-5-carboxaldehyde (1.86 g, 100 mmol) was dissolved in a mixture of methanol (10 ml) and DMF (10 ml) and triethylamine (2.75 ml, 20 mmol) was added. To this solution was added palladium (II) acetate (56 mg, 0.25 mmol) and 1,1-bis(diphenylphosphino)ferrocene (0.28 g, 0.5 mmol). The mixture was degassed by bubbling through carbon monoxide gas and was then kept under an atmosphere of carbon monoxide at atmospheric pressure using a balloon. The mixture was heated at 55° C. for 48 hours, then poured into water and extracted with ethyl acetate (100 ml). The organic phase was washed with water (×2) and brine and then dried over anhydrous sodium sulphate. The drying agent was filtered off and the solution was evaporated to dryness yielding a dark solid. This was purified by chromatography on a RediSep® Si cartridge using 0-40% ethyl acetate in DCM as eluent. Appropriate fractions were combined to yield the required product as a pale pink solid.

Yield=750 mg (45%)
$^1$H NMR (400 MHz, CDCl$_3$) δ=4.06 (s, 3H), 8.32 (m, 2H), 9.20 (m, 1H), 10.22 (s, 1H)

Intermediate 6

To a solution of polyphosphoric acid (2.9 g) in THF (20 ml) was added Intermediate 5 (0.85 g, 5.15 mmol), (3-trifluoromethylphenyl)urea (1.05 g, 5.15 mmol) and methyl acetoacetate (0.60 g, 5.15 mmol). The mixture was heated under reflux for 6 hours, then cooled to RT and the solvent removed under reduced pressure. The residue was partitioned between ethyl acetate and water. The organic layer was separated and washed with water, then brine, and finally dried over anhydrous sodium sulphate. The drying agent was filtered off and the filtrate was evaporated to dryness yielding a pale yellow foam. Purification was achieved by chromatography on a RediSep® Si cartridge using ethyl acetate as eluent. Appropriate fractions were combined to yield the required product as a colourless foam.

Yield=1.2 g (53%)
LC-MS (Method 1): Rt=4.02 min, m/z=450.35 [M+H]$^+$

Intermediate 7

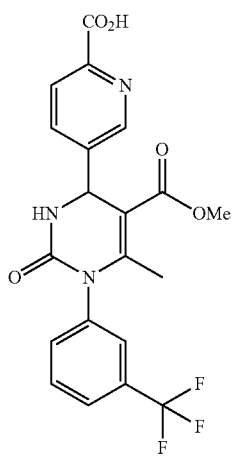 [SMILES: COC(=O)C1=C(C)N(c2cccc(C(F)(F)F)c2)C(=O)NC1c1ccc(C(=O)O)nc1]

To a solution of Intermediate 6 (1.2 g, 2.67 mmol) in THF (30 ml) was added 1M sodium hydroxide solution (3.0 ml, 3.0 mmol). The solution was stirred at RT for 4 hours. The solvent was reduced to half volume and 1M hydrochloric acid solution (12 ml) was added. The solution was extracted with DCM (3×50 ml) and the combined extracts were washed with water, then brine and finally dried over anhydrous sodium sulphate anhydrous. The drying agent was filtered and the filtrate was evaporated to dryness yielding a colourless foam.

Yield=1.11 g (95%)

LC-MS (Method 1): Rt=3.90 min, m/z=436.33 [M+H]$^+$

Intermediate 8

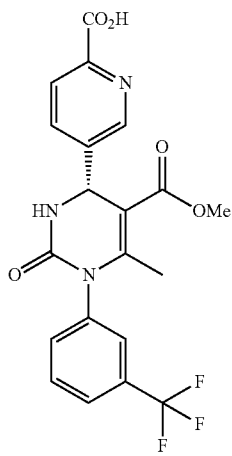 [SMILES: COC(=O)C1=C(C)N(c2cccc(C(F)(F)F)c2)C(=O)N[C@@H]1c1ccc(C(=O)O)nc1]

Intermediate 7 (1.1 g, 2.52 mmol) and (+)-cinchonine (740 mg, 2.52 mmol) were dissolved in hot ethanol (6.5 ml). The solution was allowed to cool to RT overnight and the crystalline solid filtered off (0.78 g, 84% of theory). This salt was suspended in 1N HCl (20 ml) and extracted into ethyl acetate (3×20 ml). The combined extracts were dried over magnesium sulfate, filtered and evaporated to give a white foam.

Yield=370 mg (67%)

HPLC (Chiral LC Method 3): Rt=24.5 min. This corresponded with the second eluting enantiomer when compared with the racemic mixture (Rt=15 min and 24.5 min)

Stereochemistry confirmed by conversion into Intermediate 3a via Intermediate 9.

Intermediate 9

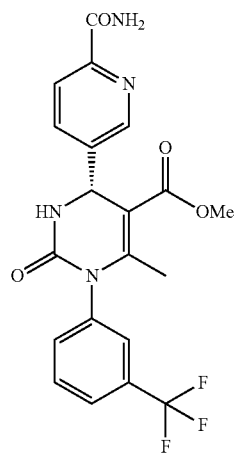 [SMILES: COC(=O)C1=C(C)N(c2cccc(C(F)(F)F)c2)C(=O)N[C@@H]1c1ccc(C(N)=O)nc1]

Intermediate 8 (0.92 g, 2.11 mmol) was dissolved in THF (10 ml) and 1,1-carbonyl diimidazole (0.69 g, 4.22 mmol) was added. This solution was left to stir at RT for 2 hours, then 33% aqueous ammonia solution (10 ml) was added and the mixture was stirred for a further 30 min. After this time, water (25 ml) was added and the product was extracted into ethyl acetate. The organic phase was washed with water (×2), then with brine and dried over anhydrous sodium sulphate. The drying agent was filtered off and the solution was evaporated to dryness yielding a colourless foam.

Yield=0.84 g (93%)

LC-MS (Method 2): Rt=3.90 min, m/z=435 [M+H]$^+$

Stereochemistry confirmed by conversion into Intermediate 3a.

Intermediate 10

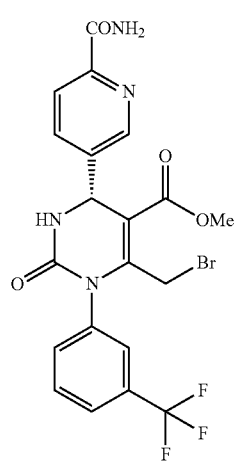 [SMILES: COC(=O)C1=C(CBr)N(c2cccc(C(F)(F)F)c2)C(=O)N[C@@H]1c1ccc(C(N)=O)nc1]

Intermediate 9 (0.84 g, 1.93 mmol) was dissolved in chloroform. A solution of bromine (0.48 g, 3.48 mmol) in chloroform (2 ml) was added to the stirred suspension over 10 min, and then the mixture was left to stir at RT for 30 min. The solvent was removed by evaporation under reduced pressure and the residue was partitioned between ethyl acetate and 10% aqueous potassium carbonate solution. The organic phase was washed with water, then with brine and finally dried over anhydrous sodium sulphate. The drying agent was filtered off and the filtrate was evaporated to dryness.

Yield=0.93 g (94%)

LC-MS (Method 2): Rt=3.61 min, m/z=513/515 [M+H]+

Intermediate 11

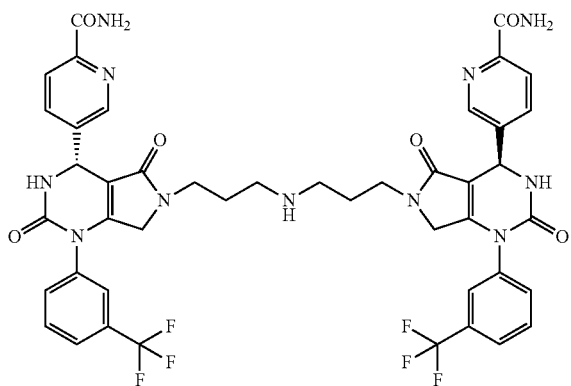 [SMILES: NC(=O)c1ccc([C@H]2NC(=O)N(c3cccc(C(F)(F)F)c3)C3=C2C(=O)N(CCCNCCCN2CC4=C(C2=O)[C@@H](c2ccc(C(N)=O)nc2)NC(=O)N4c2cccc(C(F)(F)F)c2)C3)cn1]

Intermediate 10 (0.93 g, 1.81 mmol) was dissolved in THF (15 ml) and triethylamine (1.0 ml, 7.24 mmol) was added, followed by bis-(3-aminopropyl)amine (0.25 ml, 1.81 mmol). The mixture was left to stand at RT for 24 hours, then the solvent was removed and the residue was purified by chromatography using a RediSep® Si cartridge and 0-15% 2M ammonia in methanol/DCM as eluent. The appropriate fractions were combined to yield the required product as a pale foam.

Yield: 420 mg (50%)

LC-MS (Method 2): Rt=2.30 min, m/z=932.34 [M+H]+

Compound (IA) and Salts 1-5

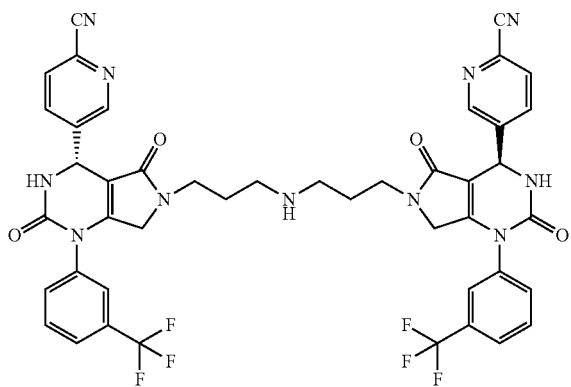 [SMILES: N#Cc1ccc([C@H]2NC(=O)N(c3cccc(C(F)(F)F)c3)C3=C2C(=O)N(CCCNCCCN2CC4=C(C2=O)[C@@H](c2ccc(C#N)nc2)NC(=O)N4c2cccc(C(F)(F)F)c2)C3)cn1]

Method 1

To a solution of Intermediate 4 (54.0 g, 109 mmol) in THF (650 ml) was added triethylamine (43.7 ml, 436 mmol) and the solution stirred at 25° C. under nitrogen. Bis-(3-aminopropyl)amine (14.3 g, 2.28 ml, 109 mmol) was dissolved in THF (50 ml) and added to the solution in one portion. The mixture was then stirred at 25° C. for 22 hours. The reaction solution was reduced in volume to ca.150 ml and partitioned between ethyl acetate (1 l) and water (500 ml). The layers were separated and the aqueous layer was re-extracted with ethyl acetate (200 ml). The combined organic layers were washed with water (500 ml) and brine (500 ml) and then dried over sodium sulphate. The solution was filtered and the filtrate evaporated to dryness yielding 53.0 g of a pale foam. The foam was dissolved in 10% MeOH/EtOAc (500 ml) and a solution of 4-toluenesulphonic acid monohydrate (11.0 g, 58 mmol) in 10% MeOH/EtOAc (50 ml) was added. The clear solution was stirred for 2 hours, during which time the tosylate salt (Salt 1) was precipitated as a colourless crystalline solid. This was then filtered off, washed well with 10% MeOH/EtOAc and dried at 3 mbar at 45° C.

Yield=37.35 g (64%)

The salt (15 g) was re-crystallised from MeOH and the white crystalline product was filtered, washed with a little cold MeOH and dried in vacuo at 45° C.

Recovery=10 g m.p.=188-190° C.

LC-MS (Method 3): Rt=7.46 min, m/z=896.39 [M+H]+ and Rt=3.26, m/z=171.10 [TsO]−

$^1$H NMR (400 MHz, $d_6$-DMSO) δ=1.59 (m, 4H), 2.96 (s, 3H), 2.65 (m, 4H), 3.09-3.27 (m, 4H), 3.78 (m, 4H), 5.55 (d, 2H), 7.06 (m, 2H), 7.42 (m, 2H), 7.65-7.80 (m, 6H), 7.92 (br s, 2H), 7.96-8.09 (m, 4H), 8.13 (dd, 2H), 8.20 (d, 2H), 8.84 (d, 2H)

Optical rotation $[α]_D^{25}$-58.3°

Stereochemistry confirmed as (R, R) by X-ray crystal structure of Intermediate 4.

Hygroscopicity

Desorption (change in mass (%)—ref @25° C. and 80% RH)=3.6

DSC analysis—Single melting endotherm onsetting at about 185° C.

XRPD (System 1). The eight major peaks (defined as those having the highest relative intensities) of the XRPD diffraction pattern characterising the crystalline 4-methylbenzenesulphonate salt of compound IA are, in degrees 2θ: between 6.15 and 6.25; between 18.59 and 18.69; between 17.59 and 17.69; between 12.30 and 12.40; between 16.70 and 16.80; between 24.90 and 25.00; between 21.67 and 21.77; and between 13.55 and 13.65. In this assessment the peaks were at (degrees 2θ) 6.20, 18.64, 17.64, 12.35, 16.75, 24.95, 21.72, and 13.60.

Method 2

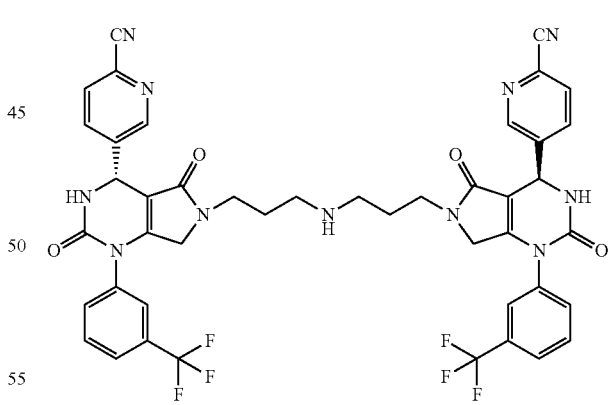

Intermediate 11 (420 mg, 0.45 mmol) was dissolved in DMF (6 ml) and the solution cooled to 0-5° C. in an ice bath. Phosphorus oxychloride (0.2 ml, 2.14 mmol) was added dropwise and the solution allowed to stir at 0-5° C. for 15 min. The solution was then poured into a mixture of ice and water and allowed to warm up to RT. The pH was adjusted to 8-9 with dilute potassium carbonate solution and the solid product was filtered off, washed well with water and dried in vacuo.

Yield=185 mg (46%)

LC-MS (Method 2): Rt=2.51 min, m/z=896.53 [M+H]$^+$

The product from this reaction (185 mg) was dissolved in 10% methanol/ethyl acetate (2 ml) and 4-toluenesulphonic acid (40 mg, 1.02 equivalents) was added. The solution was stirred at RT overnight and the precipitated salt was filtered off, washed with a little 10% methanol/ethyl acetate, and dried in vacuo at 50° C.

Yield=95 mg (44%)

LC-MS (Method 4): Rt=3.56 min, m/z=896.35

Optical rotation $[\alpha]_D^{25}$ −55.3°

Stereochemistry confirmed as (R, R) by comparison with compound IA prepared by Method 1.

Salts 2-5

To a solution/suspension of the acid (1.1 equivalents) in solvent (0.5 ml) was added a solution of compound IA (100 mg, 0.11 mmol) in the same solvent (1 ml) with stirring. The mixtures were stirred at RT overnight. The salt was filtered, washed with a small amount of cold solvent, and dried in vacuo.

| Salt | Acid | Solvent | Hygroscopicity* |
|---|---|---|---|
| 2 | Sulphuric | MeOH | 7.8 |
| 3 | Benzenesulfonic | THF | 5.6 |
| 4 | 2,5-Dihydroxybenzoic | THF | 3.7 |
| 5 | Fumaric | MeCN | 3.0 |

*Desorption (change in mass (%) - ref @80% RH)

Salt 2

1H NMR (400 MHz, d$_6$-DMSO) δ=1.59 (m, 4H), 2.65 (m, 4H), 3.09-3.27 (m, 4H), 3.78 (m, 4H), 5.55 (d, 2H), 7.65-7.80 (m, 6H), 7.92 (br s, 2H), 7.96-8.09 (m, 4H), 8.13 (dd, 2H), 8.20 (d, 2H), 8.84 (d, 2H)

DSC—Did not melt before decomposition at approximately 240° C.

XRPD (System 2)—The eight major peaks (defined as those having the highest relative intensities) of the XRPD diffraction pattern characterising the crystalline hydrogen sulphate salt of compound IA are, in degrees 2θ: between 6.38 and 6.48; between 17.78 and 17.88; between 13.95 and 14.05; between 19.36 and 19.46; between 17.29 and 17.39; between 12.81 and 12.91; between 20.18 and 20.28; and between 22.03 and 22.13. In this assessment the peaks were at (degrees 2θ) 6.43, 17.83, 14.00, 19.41, 17.34, 12.86, 20.23 and 22.08.

Salt 3

1H NMR (400 MHz, d$_6$-DMSO) δ=1.59 (m, 4H), 2.65 (m, 4H), 3.09-3.27 (m, 4H), 3.78 (m, 4H), 5.55 (d, 2H), 7.23-7.30 (m, 3H), 7.52-7.57 (m, 2H), 7.65-7.80 (m, 6H), 7.92 (br s, 2H), 7.96-8.09 (m, 4H), 8.13 (dd, 2H), 8.20 (d, 2H), 8.84 (d, 2H)

DSC—Single melting endotherm onsetting at about 160° C.

XRPD (System 2)—The eight major peaks (defined as those having the highest relative intensities) of the XRPD diffraction pattern characterising the crystalline benzenesulfonate salt of compound IA are, in degrees 2θ: between 6.23 and 6.33; between 17.63 and 17.73; between 21.65 and 21.75; between 17.01 and 17.11; and between 18.94 and 19.04; between 22.10 and 22.20; between 19.59 and 19.69; and between 25.20 and 25.30. In this assessment the peaks were at (degrees 2θ) 6.28, 17.68, 21.70, 17.06, 18.99, 22.15, 19.64 and 25.25.

Salt 4

1H NMR (400 MHz, d$_6$-DMSO) δ=1.59 (m, 4H), 2.65 (m, 4H), 3.09-3.27 (m, 4H), 3.78 (m, 4H), 5.55 (d, 2H), 6.43 (d, 1H), 6.59 (dd, 1H), 7.09 (d, 1H), 7.65-7.80 (m, 6H), 7.92 (br s, 2H), 7.96-8.09 (m, 4H), 8.13 (dd, 2H), 8.20 (d, 2H), 8.84 (d, 2H)

DSC—single melting endotherm onset at about 178° C.

XRPD (System 2)—The eight major peaks (defined as those having the highest relative intensities) of the XRPD diffraction pattern characterising the crystalline 2,5-dihydroxybenzoate salt of compound IA are, in degrees 2θ: between 22.70 and 22.80; between 11.26 and 11.36; between 16.46 and 16.56; between 21.74 and 21.84; between 23.16 and 23.26; between 18.63 and 18.73; between 16.96 and 17.06; and between 20.64 and 20.74. In this assessment the peaks were at (degrees 2θ) 22.75, 11.31, 16.51, 21.79, 23.21, 18.68, 17.01, 20.69.

Salt 5

1H NMR (400 MHz, d$_6$-DMSO) δ=1.59 (m, 4H), 2.65 (m, 4H), 3.09-3.27 (m, 4H), 3.78 (m, 4H), 5.55 (d, 2H), 6.42 (s, 2H), 7.65-7.80 (m, 6H), 7.92 (br s, 2H), 7.96-8.09 (m, 4H), 8.13 (dd, 2H), 8.20 (d, 2H), 8.84 (d, 2H)

DSC—Single/double melting endotherm onsetting at about 176° C.

XRPD (System 2)—The eight major peaks (defined as those having the highest relative intensities) of the XRPD diffraction pattern characterising the crystalline fumarate salt of compound IA are, in degrees 2θ: between 23.68 and 23.78; between 22.51 and 22.61; between 5.76 and 5.86; between 11.75 and 11.85; between 10.10 and 10.20; between 20.32 and 20.42; between 21.17 and 21.27; and between 24.64 and 24.74. In this assessment the peaks were (degrees 2θ) 23.73, 22.56, 5.81, 11.80, 10.15, 20.37, 21.22, 24.69.

B. Biological Assays

The compound of Example 18 of WO2007/129060 has the structural formula (II).

(II)

Compound (II) differs in structure from compound (I) of the invention in that cyano substituted phenyl rings are present in (II) whereas cyano-substituted pyridyl rings are present in (I).

Compound (II) was prepared as in Example 18 of WO2007/129060 and was tested alongside the compound (IA) of the invention in the following assays. Both compounds were tested as the free base:

Enzyme Inhibition Assays

Using Fluorescent Peptide Substrate

Assays were performed in 96-well plates at a total assay volume of 100 μl. The final concentration of the enzyme (human leukocyte elastase, Sigma E8140) was 0.00036 units/ well. A peptide substrate (MeO-Suc-Ala-Ala-Pro-ValAMC (SEQ ID NO: 1), Calbiochem #324745) was used, at the final concentration of 100 µM. The final concentration of DMSO was 1% in the assay buffer (0.05M Tris.HCl, pH 7.5, 0.1M NaCl; 0.1M CaCl2; 0.0005% brij-35).

The enzymatic reaction was started by adding the enzyme. The enzymatic reaction was performed at RT and after 30 mins stopped by adding 50 µl soybean trypsin inhibitor (Sigma T-9003) at a final concentration of 50 µg/well. Fluorescence was read on the FLEXstation (Molecular Devices) using 380 nm excitation and 460 nm emission filters. The potency of the compounds was determined from a concentration series of 10 concentrations in range from 1000 nM to 0.051 nM. The results are means of two independent experiments, each performed in duplicate.

The results are means of two independent experiments, each performed in duplicate.

The $IC_{50}$s of Compounds (IA) and (II) in the above assay were 8.4 nM and 2.1 nM, respectively.

HNE Induced Lung Haemorrhage in the Rat

Instillation of human neutrophil elastase (HNE) into rat lung causes acute lung damage. The extent of this injury can be assessed by measuring lung haemorrhage.

Male Sprague Dawley rats (175-220 g) were obtained from Harlan UK Ltd., full barrier-bred and certified free from specified micro-organisms on receipt. Animals were weighed and randomly assigned to treatment groups (7-12 animals to per group).

The vehicle used was 1% DMSO/Saline. Inhibitors were dissolved in 1% DMSO before the addition of 0.9% saline.

Animals in each study used to determine the efficacy of the elastase inhibitors delivered locally to the lung by a variety of routes. Rats were anaesthetised with the inhaled anaesthetic Isoflurane (4%) when the dose was given from 30 minutes to 6 h prior to human neutrophil elastase (HNE) administration or terminally anaesthetised with hypnorm:hypnovel:water (1.5:1:2 at 2.7 ml/kg) when the predose was given at less than 30 minutes prior to HNE administration and dosed either intratracheally (i.t.) by transoral administration using a Penn Century microsprayer or intranasally (i.n.) by dropping the fluid on to the nares. Animals either received vehicle or compound at a dose volume of 0.5 ml/kg.

Animals that had been allowed to recover after dosing were terminally anaesthetised with hypnorm:hypnovel:water (1.5:1:2 at 2.7 ml/kg). Once sufficiently anaesthetised, HNE (600 units/ml) or sterile saline was administered by transoral tracheal instillation at a volume of 100 µl using a Penn Century microsprayer. Animals were kept warm in a temperature controlled box and given top up doses of anaesthetic as required to ensure continuous anaesthesia until termination.

Animals were sacrificed (0.5 ml to 1 ml sodium pentobarbitone) one hour post HNE challenge. The trachea was exposed and a small incision made between two tracheal rings allowing a cannula (10 gauge, O.D. 2-10 mm, Portex Ltd.) to be inserted approximately 2 cm into the trachea towards the lung. This was secured into place with a cotton ligature. The lungs were then lavaged (BAL) three times with fresh 4 ml aliquots of heparinised (10 units/ml) phosphate buffered saline (PBS). The resultant BALF was kept on ice until it was centrifuged.

The BALF was centrifuged at 1000 r.p.m. for 10 minutes in a centrifuge cooled to between 4 and 10° C. The supernatant was discarded and the cell pellet resuspended in 1 ml 0.1% CETAB/PBS to lyse the cells. Cell lysates were frozen until spectrophotometric analysis for blood content could be made. Standards were prepared by making solutions of whole rat blood in 0.1% CETAB/PBS.

Once defrosted 100 µl of each lysed cell suspension was placed into a separate well of a 96 well flat bottomed plate. All samples were tested in duplicate and 100 µl 0.1% CETAB/PBS was included on the plate as a blank. The OD of the contents of each well was measured at 415 nm using a spectramax 250 (Molecular devices).

A standard curve was constructed by measuring the OD (at 415 nm) of different concentrations of blood in 0.1% CETAB/PBS (30, 10, 7, 3, 1, 0.3, 0.1 µl/ml).

The amount of blood in each experimental sample was calculated by comparison to the standard curve. Data were then analysed as below:
1) The mean OD for duplicates was calculated
2) The value for the blank was subtracted from the value for all other samples
3) Data were assessed to evaluate the normality of distribution.

Compound (IA) and (II) showed a statistically significant reduction in haemorrhage of 95% and 88% respectively relative to control when administered at 100 µg/kg i.t, 6 hours prior to HNE.

Comparison of the Half Lives in the Lung of the Compound of the Invention and the Compound of Example 18 of WO2007/129060

PK Assay

Test material was formulated at 20 µg/mL in 0.2% Tween 80 in saline. Solutions were sonicated and warmed in a water bath at 40° C. prior to dosing. Male Sprague-Dawley rats received a single intra-tracheal administration of the test material via a Penn-Century dosing needle at the nominal dose level of 10 µg/Kg. After dosing five rats from each group were terminally anaesthetized with sodium pentobarbitone at 1, 2, 4, 8, 24, 72 and 96 hours for compound (IA) (free base) and 1, 4, 8, 24, 72, 96, 168, 264 and 336 for compound (II) (free base) post dose. Blood was sampled from the tail vein, following which the chest was opened, the animal exanguinated by perfusion and the lungs removed and snap frozen. After collection the blood samples were centrifuged (10000× g, 2 min at 4° C.). Plasma was removed and both stored frozen at −20° C. Rat lungs were homogenised in water (on ice) to give a ratio of 1 part lung:2 parts water (w/v). A 100 µL aliquot of each homogenate was extracted by addition of 200 µL acetonitrile containing an analytical internal standard. Following vortex mixing and centrifugation (10000×g, 5 min at 4° C.), a 100 µL aliquot of supernatant was combined with 50 µL water in a low volume LC vial. The samples were thoroughly mixed and assayed for test compounds by LCMSMS against a series of matrix matched calibration curve standards, prepared by spiking control rat lung homogenate and extracting 1000 µL aliquots using the method described for the samples above.

Test material was analysed on a triple quadrupole mass spectrometer (AB Sciex API 3000) fitted with LC pump and autosampler (Reliance). Test material was detected in positive ion mode Turbo Ion Spray. Analytical separation of test material was facilitated on a reverse-phase C18 5 µm analytical column (Higgins, Clipeus, 50×3 mm) using a mobile phase of 0.5% formic acid, water and acetonitrile at a flow rate of 1 mL/min. The initial conditions consisted of 0.5% formic acid in 90% water, 10% acetonitrile which were held for 1 minute prior initiating a linear gradient. The water content of the mobile phase decreased to 10% over 2 minutes with a concomitant increase in acetonitrile. The final conditions were held for a further 1 minute before returning to initial conditions.

The observed terminal lung $t_{1/2}$, of the compound (IA) of the invention was 37 h with 80% confidence interval of 31-46 h. This was significantly shorter than the comparison compound Example 18 of WO2007/129060, which had a terminal lung $t_{1/2}$ of 94 h with 80% confidence intervals of 85-104 h.

The invention claimed is:

1. A compound of formula (I):

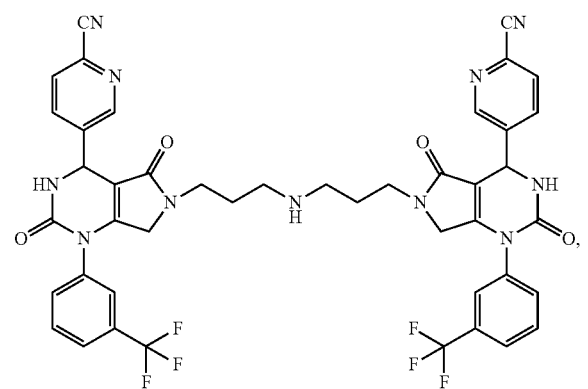

(I)

or a pharmaceutically acceptable salt thereof.

2. A compound or salt of claim 1 wherein the R-R stereo-configuration, shown in formula (IA), predominates over at least one configuration selected from the group consisting of the R-S configuration and the S-S configuration:

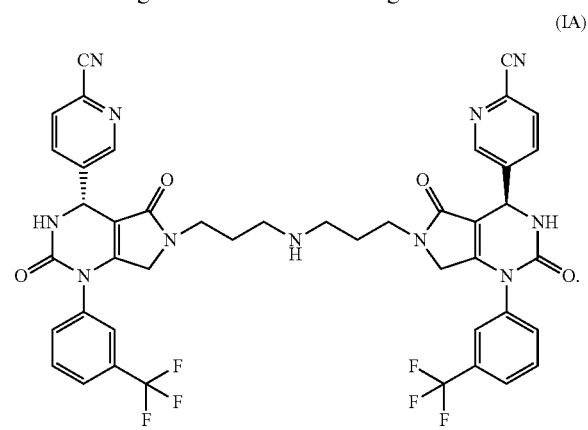

(IA)

3. A pharmaceutical composition, comprising:
the compound or salt of claim 1; and
one or more pharmaceutically acceptable carriers or excipients,
wherein the composition is adapted for delivery to the lungs by inhalation.

4. A method of manufacturing an inhalable composition, comprising:
combining a compound or salt of claim 1 with the inhalable composition.

5. A method of treatment of a disease selected from the group consisting of chronic obstructive pulmonary disease (COPD), chronic bronchitis, lung fibrosis, pneumonia, acute respiratory distress syndrome (ARDS), pulmonary emphysema, smoking-induced emphysema, and cystic fibrosis, in a subject suffering from such disease, the method comprising:
administering to the subject, by pulmonary inhalation, an effective amount of a compound or salt of claim 1.

6. A compound or salt of claim 1 wherein the R-R stereo-configuration, shown in formula (IA), predominates over the R-S configuration:

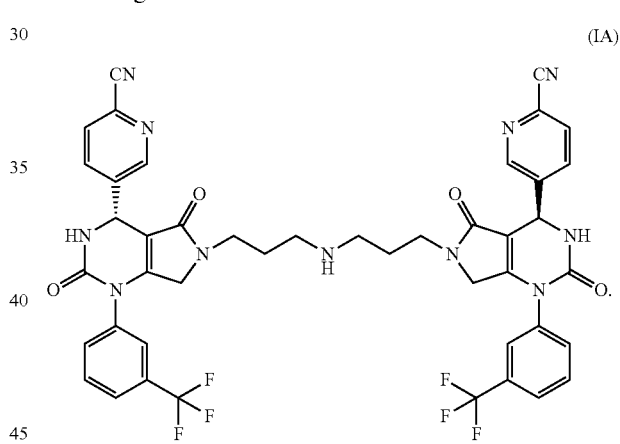

(IA)

7. A compound or salt of claim 1 wherein the R-R stereo-configuration, shown in formula (IA), predominates over the S-S configuration:

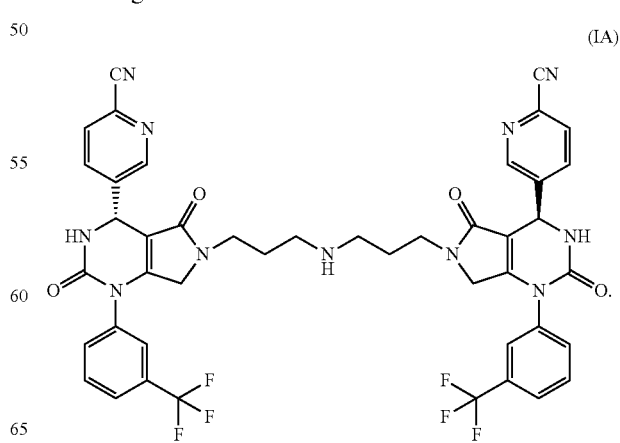

(IA)

8. A compound or salt of claim 1 wherein the R-R stereo-configuration, shown in formula (IA), predominates over the R-S configuration and the S-S configuration:

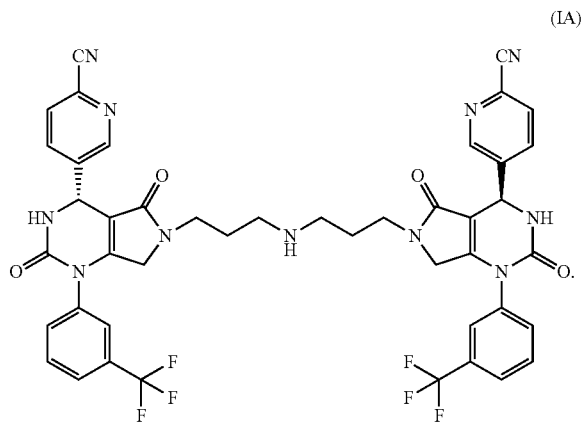 [SMILES: N#Cc1ccc([C@H]2NC(=O)N(c3cccc(C(F)(F)F)c3)C3=C2C(=O)N(CCCNCCCN2CC4=C(C2=O)[C@@H](c2ccc(C#N)nc2)NC(=O)N4c2cccc(C(F)(F)F)c2)C3)cn1]

(IA)

9. A pharmaceutical composition, comprising:
a compound or salt of claim 2; and
one or more pharmaceutically acceptable carriers or excipients,
wherein the composition is adapted for delivery to the lungs by inhalation.

10. A method of manufacturing an inhalable composition, comprising:
combining a compound or salt of claim 2 with the inhalable composition.

11. A method of treatment of a disease selected from the group consisting of chronic obstructive pulmonary disease (COPD), chronic bronchitis, lung fibrosis, pneumonia, acute respiratory distress syndrome (ARDS), pulmonary emphysema, smoking-induced emphysema, and cystic fibrosis, in a subject suffering from such disease, the method comprising: administering to the subject, by pulmonary inhalation, an effective amount of a compound or salt of claim 2.

12. A compound or salt of claim 2, wherein at least 90% by weight of the R-R diastereomer and less than 10% by weight respectively of other diastereomers are present.

13. A compound or salt of claim 2, wherein at least 95% by weight of the R-R diastereomer and less than 5% by weight respectively of other diastereomers are present.

14. A compound or salt of claim 2, wherein at least 98% by weight of the R-R diastereomer and less than 2% by weight respectively of other diastereomers are present.

15. A composition of claim 3, wherein the compound or salt is in the form of at least one microparticle.

16. A composition of claim 15, further comprising a carrier particle.

17. A composition of claim 3, in the form of a suspension, suitable for delivery from a nebulizer.

18. A composition of claim 3, in the form of aerosol in a liquid propellant, suitable for a pressurized metered dose inhaler (PMDI).

19. A composition of claim 3, in the form of a dry powder, suitable for delivery with a dry powder inhaler (DPI).

20. A composition of claim 3, further comprising at least one therapeutic agent selected from the group consisting of:
a corticosteroid;
a β2-adrenoreceptor agonist;
a leukotriene modulator;
anticholinergic agents;
a dual muscarinic-3 (M3) receptor antagonist/β2-adrenoreceptor agonist;
a phosphodiesterase-IV (PDE-IV) inhibitor;
an antitussive agent;
a non-steroidal anti-inflammatory agent (NSAID);
a mucolytic;
a expectorant/mucokinetic modulator;
a peptide mucolytic; and
an antibiotic.

* * * * *

SEQUENCE LISTING

```
<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ala Ala Pro Val
1
```